(12) United States Patent
Farhadi et al.

(10) Patent No.: US 8,728,090 B2
(45) Date of Patent: May 20, 2014

(54) TONSILLAR SUCTION DISSECTOR

(76) Inventors: Mohamad Farhadi, Tehran (IR); Hadi ghanbari, Tehran (IR)

( * ) Notice: Subject to any disclaimer, the term of this patent is extended or adjusted under 35 U.S.C. 154(b) by 20 days.

(21) Appl. No.: 13/348,655

(22) Filed: Jan. 12, 2012

(65) Prior Publication Data

US 2013/0184717 A1 Jul. 18, 2013

(51) Int. Cl.
*A61B 17/26* (2006.01)

(52) U.S. Cl.
USPC .......................................................... 606/115

(58) Field of Classification Search
USPC ......... 606/110–115, 127, 128, 159–162, 167, 606/170, 190
See application file for complete search history.

(56) References Cited

U.S. PATENT DOCUMENTS

| 3,308,825 | A | * | 3/1967 | Cruse | 604/267 |
|---|---|---|---|---|---|
| 3,495,593 | A | * | 2/1970 | Snyder | 606/115 |
| 4,767,404 | A | * | 8/1988 | Renton | 604/48 |
| 5,358,507 | A | * | 10/1994 | Daily | 606/159 |
| 5,522,826 | A | * | 6/1996 | Daily | 606/159 |
| 5,603,712 | A | * | 2/1997 | Koranda et al. | 606/51 |
| 6,086,587 | A | * | 7/2000 | Hawk | 606/53 |
| 8,157,832 | B2 | * | 4/2012 | Refai | 606/190 |
| 2005/0171467 | A1 | * | 8/2005 | Landman | 604/35 |
| 2006/0212056 | A1 | * | 9/2006 | Salvadori et al. | 606/167 |
| 2010/0312186 | A1 | * | 12/2010 | Suchdev et al. | 604/131 |
| 2012/0197279 | A1 | * | 8/2012 | Perez-Cruet et al. | 606/170 |
| 2012/0310268 | A1 | * | 12/2012 | Whayne et al. | 606/190 |

* cited by examiner

*Primary Examiner* — Ryan Serverson
(74) *Attorney, Agent, or Firm* — Patent 360 LLC; Barry Choobin

(57) ABSTRACT

The various embodiments of the present invention provide a tonsillar suction dissector for performing the functions of dissecting a tonsil and suctioning blood simultaneously. The tonsillar suction dissector includes a handle, a suction tube connected to one end of the handle, a proximal part coupled to a proximal end, a serrated distal end connected to the proximal part through the suction tube, a rolling part interconnected to the proximal part and the proximal end, and a tip assembly. The opening suctioning channels placed adjacent to the serrated distal end provide an opening to communicate with the handle and allows the suction tube to suction to clear a dissection surface thereby performing the functions of dissecting a tonsil and suctioning the dissection surface simultaneously.

12 Claims, 2 Drawing Sheets

TONSILLAR SUCTION DISSECTOR

BACKGROUND

1. Technical Field

The embodiments herein generally relate to a surgical device and particularly relates to a dissector device for dissection of tissues at confined spaces. The embodiments herein more particularly relates to a tonsillar suction dissector for simultaneous dissection of tonsil and suction of materials at dissection area.

2. Description of the Related Art

Tonsillectomy is a surgical procedure to remove the infected tonsils in order to treat a disease state involving an infection of the tonsils. Tonsillectomy generally includes two distinct stages. One is the exposure stage in which the tonsils are exposed by cutting through the mucous membrane and muscle tissue which conceals the tonsils. The second stage is the dissection stage, in which the tonsils are freed from the underlying muscle bed and removed. During the dissection of the tonsils, the surgical device may damage the underlying muscle bed and this may result in post-operative hemorrhage and pain.

In the current scenario, the surgical devices used by the surgeons can only dissect the tonsils and another instrument need to be inserted into the dissection area if suction of blood and other materials are required. Also, the significant bleeding that occurs during dissection cannot be controlled by the existing surgical devices.

Hence there is a need for the tonsillar suction dissector to provide for simultaneous blunt dissection of the tonsils simultaneously with suctioning of the dissection area. There also exists a need to provide a tonsillar suction dissector to meticulously and atraumatically dissect tonsils in a sub-capsular plane with a minimum of bleeding and mechanical injury. Further there exists a need to provide a tonsillar suction dissector which provides space for clear visualization of the dissection area to limit the operative time and to reduce the post operative pain.

The abovementioned shortcomings, disadvantages and problems are addressed herein and which will be understood by reading and studying the following specification.

OBJECTS OF THE EMBODIMENTS

The primary object of the embodiments herein is to provide a tonsillar suction dissector for performing simultaneous dissection of tonsil and suction of materials at dissection area.

Another object of the embodiments herein is to provide a surgeon with an instrument to meticulously and traumatically dissect tonsils in a true sub-capsular plane with a minimum of bleeding and mechanical injury.

Yet another object of the embodiments herein is to provide cost benefits and operative time saving, as the surgeon only needs to handle one instrument and avoid switching back and forth between two instruments.

Yet another object of the embodiments herein is to provide a tonsillar suction dissector that prevents an adequate contact with the tissue being sucked into the suction tube.

These and other objects and advantages of the present invention will become readily apparent from the following detailed description taken in conjunction with the accompanying drawings.

SUMMARY

The embodiments herein provide a tonsillar suction dissector for performing the functions of dissecting a tonsil and suctioning bleeding simultaneously. The tonsillar suction dissector includes a handle assembly, a tip assembly and a blunt dissection assembly. The handle assembly has a suction tube connected to one end of the handle. A first proximal part is coupled to the suction tube. A rolling part is connected to the first proximal part and a sharp serrated and bent tip is provided at a proximal end for dissecting a serrated distal end with opening pores connected to the suction tube. The blunt dissection assembly has a blunt edge provided with serrated edges and opening pores. The opening suctioning channels placed adjacent to the serrated distal end provide an opening to communicate with the handle and allows the suction tube to suction to clear a dissection surface thereby performing the functions of dissecting a tonsil and suctioning the dissection surface simultaneously.

According to an embodiment herein, the serrated distal end comprises one or more opening orifices. The opening orifices at the tip of the serrated distal end are co-planar with a dissection surface to perform suctioning.

According to an embodiment herein, the handle and the suction tube are aligned along a single axial shaft with the proximal part, the rolling part and the proximal end.

According to an embodiment herein, the serrated distal end is placed at an angle of 180 degree. According to an embodiment herein, the serrated distal end is semi beveled in structure.

According to an embodiment herein, the serrated distal end comprises a plurality of suction pores to regulate a suction power.

According to an embodiment herein, the tip at the proximal end performs dissection at an upper pole of the tonsil.

According to an embodiment herein, the serrated distal end has a beveled edge to perform blunt dissection.

According to an embodiment herein, the opening orifices at the tip assembly allows rapid clearing of blood from the dissection surface by performing suctioning.

According to an embodiment herein, the serrated distal end is semi beveled in structure for pushing out open tissue borders in a tight space.

According to an embodiment herein, the tonsillar suction dissector includes a tip assembly to dissect a reolar tissue of the tonsillar bed from palatine tonsils.

According to an embodiment herein, the tip assembly comprises one or more co-planar enclosed opening orifices near the end of the serrated distal end.

These and other objects and advantages of the present invention will become readily apparent from the following detailed description taken in conjunction with the accompanying drawings.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
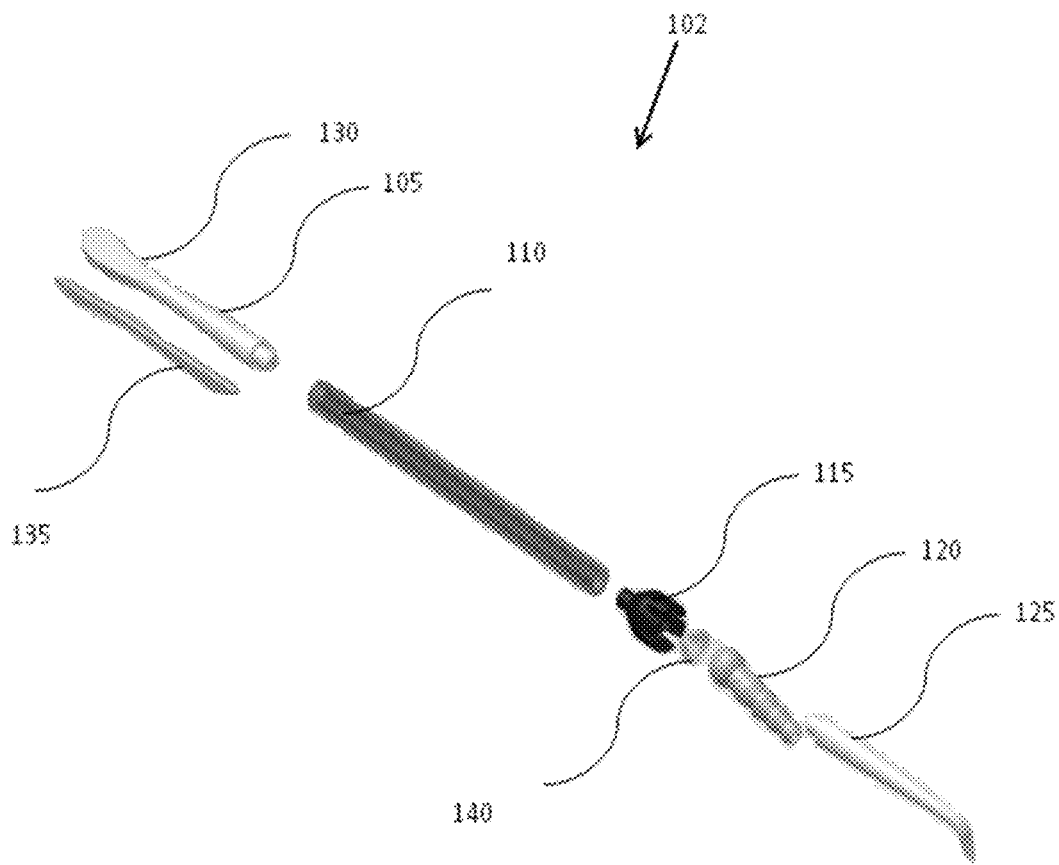
FIG. 1 illustrates an exploded perspective view of a tonsillar suction dissector, according to one embodiment herein.

Although the specific features of the embodiments herein are shown in some drawings and not in others. This is done for convenience only as each feature may be combined with any or all of the other features in accordance with the embodiment herein.

DETAILED DESCRIPTION OF THE EMBODIMENTS

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The embodiments herein provide a tonsillar suction dissector for performing the functions of dissecting a tonsil and suctioning bleeding simultaneously. The tonsillar suction dissector includes a handle, a suction tube connected to one end of the handle, a proximal part coupled to a proximal end, a serrated distal end connected to the proximal part through the suction tube, a rolling part interconnected to the proximal part and the proximal end, and a tip assembly. The opening suctioning channels placed adjacent to the serrated distal end provide an opening to communicate with the handle and allows the suction tube to suction to clear a dissection surface thereby performing the functions of dissecting a tonsil and suctioning the dissection surface simultaneously.

According to an embodiment herein, the opening orifices at the tip of the serrated distal end assembly are co-planar with a dissection surface to perform suctioning.

According to an embodiment herein, the handle and the suction tube are aligned along a single axial shaft with the proximal part, the rolling part and the proximal end.

According to an embodiment herein, the serrated distal end is connected to the dissection tool at an angle of 180 degree.

According to an embodiment herein, the serrated distal end is semi beveled in structure.

According to an embodiment herein, the serrated distal end comprises a plurality of suction pores to regulate a suction power.

According to an embodiment herein, the proximal end performs dissection at an upper pole of the tonsil.

According to an embodiment herein, the serrated distal end has a beveled edge to perform blunt dissection.

According to an embodiment herein, the opening orifices at the tip assembly allows rapid clearing of blood from the dissection surface by performing suctioning.

According to an embodiment herein, the serrated distal end is semi beveled in structure for pushing out open tissue borders in a tight space.

According to an embodiment herein, the tonsillar suction dissector includes a tip assembly to dissect areolar tissue of the tonsillar bed from palatine tonsils.

According to an embodiment herein, the tip assembly comprises one or more co-planar enclosed opening orifices near the end of the serrated distal end.

FIG. 1 illustrates an exploded view of a tonsillar suction dissector, according to one embodiment of the present disclosure. With respect to FIG. 1, a tonsillar suction dissector 102 includes a handle, a suction tube 110 connected to one end of the handle, a proximal part 115, a serrated distal end 130 connected to the proximal part 115 through the suction tube 110, a proximal end 125 and a rolling part 120 interconnected to the proximal part 115 and the proximal end 125. The tonsillar suction dissector 102 includes a silicone part 140. The handle of the tonsillar suction dissector 102 further includes a sealing 135 for opening pores. The tonsillar suction dissector also includes a tip assembly.

The tonsillar suction dissector 102 includes a fixed channel and a central metal tube that is connected to a fixed handle base. The central metal tube is the suction tube 110. Further the suction tube 110 is attached to the hollow fixed base as a port for suctioning material during surgery. The central metal tube includes a conductive metal at the inner side of the handle and an outside layer of the handle 105 surface at the exposed area.

A hollow channel formed of an inner metal allows suction to pass through the suction tube 110 to a suction port and out of the tonsillar suction dissector 102 for proper disposal. The suction tube 110 is arranged alongside the serrated distal end 130. The serrated distal end 130 contains opening suction pores to regulate suction power. The suction pores location can be modified and customized by the user depending on individual surgical circumstances. The actual serrated distal end 130 with opening pores at the base is cut at a beveled angle and placed alongside the serrated distal end 130 connected to the handle 105.

The tonsillar suction dissector 102 performs dissection and suctioning simultaneously. The first stage or an exposure stage is carried out with the sharp beveled tip of the proximal end 125 of the tonsillar suction dissector 102. The sharp edge of the proximal end 125 allows rapid cutting of the tonsils in a manner similar to traditional dissectors. Further during the dissection stage, the blunt dissection is carried out with the serrated tip.

The serrated leading edge is in a shape of an ovoid and the serrated leading edge provides an ideal pushing force to perform blunt dissection. Further the suction tube 110 is instantly suctioning the bleeding from the perforating blood vessels during the dissection stage with the opening orifice of the suction tip before bleeding obscures the field of dissection.

The opening orifices at the tip of the tonsillar suction dissector 102 allow rapid clearing of blood from the field of dissection and direct suctioning application to the site of bleeding. Further no insulation is provided around the distal circumference of the tip which allows tissue contact with the full extent of the suction tube 110. The angle of the tip positions and the suction hole are directly parallel to the plane of the bleeding site. The serrated distal end 130 is connected to the dissection tool at an angle of 180 degree.

The angled portion is disposed at a point approximately 2 centimeters from an end of the serrated distal tip of the tonsillar suction dissector 102. The tonsillar suction dissector 102 includes the tip assembly to dissect a reolar tissue of the tonsillar bed from palatine tonsils. The handle 105 is provided with a metal tubing assembly. The tip assembly includes one or more co-planar enclosed opening orifices at the serrated distal end 130. The tip assembly is placed at the serrated distal end 130 of the metal tubing assembly. The tip assembly includes a beveled metal tip that does not have a layer disposed around its periphery.

The plane of the cutting surface and the plane of the handle 105 are substantially parallel and allows surgeon to move the tonsillar suction dissector 102 in a plane directly outward from a person body with the rotation pores as desired during the operation or procedure.

The tonsillar suction dissector includes a housing to accommodate a dissection tool to dissect the tonsils. The housing is designed in a shape allowing the tonsillectomy as a surgical device to be accommodated together with a dissection tool used to dissect the tonsils without any assist to suction. The shape and size of the handle provide an optional handle gripping mechanism and can be modified based on the user requirements. Further a groove or ridge is provided for handle 105 gripping mechanism.

Figure 2:
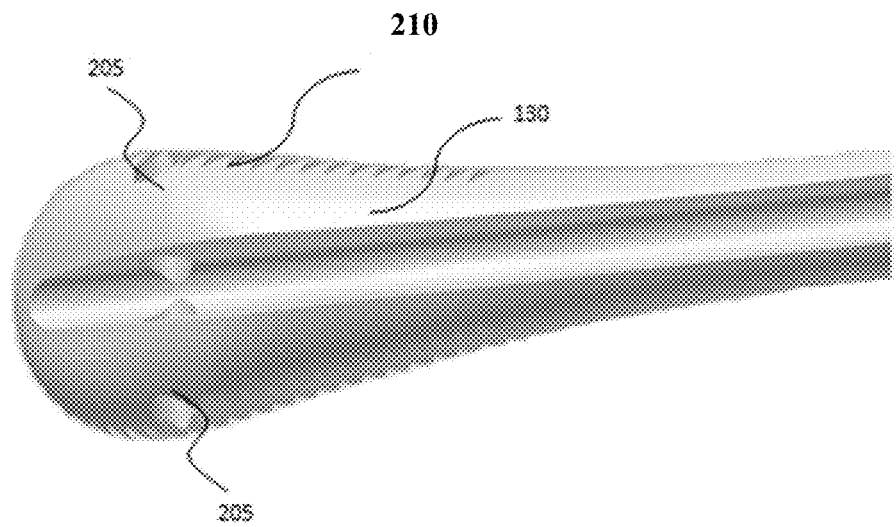
FIG. 2 illustrates a top view of a serrated distal end in a tonsillar suction dissector, according to one embodiment herein.

FIG. 2 illustrates a top view of a serrated distal end in a tonsillar suction dissector, according to one embodiment. With respect to FIG. 2, the serrated distal end 130 includes opening pores 205 and a serrated edge 210. The opening pores 205 at the tip of the tonsillar suction dissector 102 allow rapid clearing of blood from the dissection surface by performing suctioning. The suction opening orifice includes a hidden orifices terminating at the dissecting surface. The serrated distal end 130 includes a plurality of suction pores to regulate a suction power. The suction tube 110 with the suction channels forms the tubing assembly. The tubing assembly includes a main draining screwing the suction channels from the first portion to an intermediate part or the handle of the tonsillar suction dissector 102.

The opening suction channels are connected to a suction port in the handle for controlling suction of air through the opening orifice in the bottom of the surface of serrated distal end 130. The vacuum pressure in chamber of the suction tube 110 draws air through the serrated distal end 130 out and the air is further passed out through the chamber disposed in metal tubing that connects to suction port.

The serrated distal end 130 of the tonsillar suction dissector 102 includes a serrated edge 210. The serrated distal end 130 is semi beveled in structure for pushing open tissue borders in the dissection area. The serrated edge 210 is in a size of the millimeters at confined regions. The serrated edge 210 at the tip of the tonsillar suction dissector 102 is sharp enough to allow precise pinpoint cutting and suctioning at the same time. The serrated distal end 130 includes suction pores. The suction pores terminate at a convex portion beneath the distal surface connected to an intake portion of the serrated distal end 130.

The tonsillar suction dissector 102 provides an advantage of suction-tip dissecting. Further the tonsillar suction dissector 102 proposed in the embodiments herein provides a surgeon with an instrument to meticulously and traumatically dissect tonsils in a true sub-capsular plane with a minimum of bleeding and mechanical injury.

The embodiments herein provide a tonsillar suction dissector to perform dissection and suction simultaneously with a single instrument. Further this provides cost benefits and operative time saving, as the surgeon only needs to handle one instrument and avoids switching back and forth between two instruments. The tonsillar suction dissector includes a main shaft that interconnects one or more components and extends to the full length of the tube. The full length of the tube prevents an adequate contact with the tissue being sucked into the suction tube.

The foregoing description of the specific embodiments herein will so fully reveal the general nature of the embodiments herein that others can, by applying current knowledge, readily modify and/or adapt for various applications such specific embodiments herein without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the embodiments herein with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A tonsillar suction dissector comprising: a handle;
 a suction tube connected to one end of the handle;
 a proximal part coupled to the suction tube;
 a rolling part connected to the proximal part;
 a sharp serrated tip provided at a proximal end and connected to the rolling part;
 a serrated blunt distal end connected to the handle;
 multiple open suctioning channels provided adjacent to the serrated blunt distal end, wherein the open suctioning channels placed adjacent to the serrated blunt distal end provide an opening to communicate with the handle and allows the suction tube to suck liquids and dissected materials at a dissection surface to clean the dissection surface thereby performing the functions of dissecting a tonsil and suctioning the dissection surface simultaneously.

2. The tonsillar suction dissector according to claim 1, wherein the serrated blunt distal end comprises one or more opening orifices.

3. The tonsillar suction dissector according to claim 2, wherein the opening orifices at a tip of the serrated blunt distal end are co-planar with said dissection surface to perform a suctioning process.

4. The tonsillar suction dissector according to claim 1, wherein the serrated blunt distal end is semi beveled in structure.

5. The tonsillar suction dissector according to claim 1, wherein the serrated blunt distal end comprises a plurality of suction pores to regulate a suction power.

6. The tonsillar suction dissector according to claim 1, wherein the proximal end is adapted to performs dissection at an upper pole of the tonsil.

7. The tonsillar suction dissector according to claim 1, wherein the serrated blunt distal end includes a beveled edge to perform a blunt dissection.

8. The tonsillar suction dissector according to claim 1, wherein the sharp serrated tip comprises one or more co-planar opening orifices near the end of the serrated blunt distal end.

9. The tonsillar suction dissector according to claim 1, wherein opening orifices at the sharp serrated tip allow rapid clearing of blood from the dissection surface by performing a suction process.

10. The tonsillar suction dissector according to claim 1, wherein the serrated blunt distal end is semi beveled in structure for pushing out open tissue borders in a tight space.

11. The tonsillar suction dissector according to claim 1, wherein the sharp serrated tip is adapted to dissects a reolar tissue of the tonsillar bed from palatine tonsils.

12. The tonsillar suction dissector according to claim 1, wherein the handle comprises a metal tubing assembly.

* * * * *